United States Patent [19]
Chaumette et al.

[11] Patent Number: 5,171,920
[45] Date of Patent: Dec. 15, 1992

[54] PROCESS FOR OBTAINING AT LEAST ONE TERTIARY OLEFIN BY DECOMPOSITION OF THE CORRESPONDING ETHER

[75] Inventors: Patrick Chaumette, Bougival; Germain Martino, Poissy; Catherine Verdon, Rueil Malmaison; Serge Leporq, Mantes la Ville, all of France

[73] Assignee: Institut Francais du Petrole, Rueil-Malmaison, France

[21] Appl. No.: 682,290

[22] Filed: Apr. 9, 1991

[30] Foreign Application Priority Data

Apr. 9, 1991 [FR] France .................. 90 04498

[51] Int. Cl.$^5$ .................. C07C 1/20
[52] U.S. Cl. .................. 585/640; 585/638; 585/639
[58] Field of Search .............. 585/640, 639; 502/340, 502/344

[56] References Cited

U.S. PATENT DOCUMENTS 4,254,296 3/1981 Manara et al. .................. 585/640
4,343,959 8/1982 Kida et al. .................. 585/640
4,691,073 9/1987 Michaelson .................. 585/639

FOREIGN PATENT DOCUMENTS 0050992 5/1982 European Pat. Off. .
0055837 3/1984 Japan .
8700166 1/1987 PCT Int'l Appl. .

Primary Examiner—Anthony McFarlane
Assistant Examiner—P. Achutamurthy
Attorney, Agent, or Firm—Millen, White, Zelano and Branigan

[57] ABSTRACT

A process for obtaining a tertiary olefin, e.g. isobutylene in a very pure state by decomposing the corresponding ether, e.g. methyl tert. butyl ether, in the presence of a catalyst constituted by silica, modified by the addition of at least one element or compound of an element preferably chosen from the group constituted by rubidium, cesium, magnesium, calcium, strontium, barium, gallium, lanthanum, cerium, praseodymium, neodymium and uranium and optionally by the addition of at least one element or compound of an element chosen from the group constituted by aluminium, titanium and zirconium.

12 Claims, No Drawings

PROCESS FOR OBTAINING AT LEAST ONE TERTIARY OLEFIN BY DECOMPOSITION OF THE CORRESPONDING ETHER

BACKGROUND OF THE INVENTION

The present invention relates to a process for obtaining at least one very pure tertiary olefin by decomposing the corresponding ether in the presence of at least one silica-based catalyst optionally in the absence of water vapor.

The tertiary olefins obtained according to the present invention are in accordance with the formula

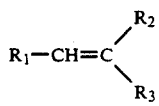

and are prepared from the corresponding ethers of formula

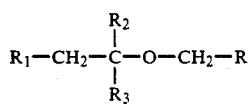

in which R and $R_1$, which can be the same or different, are in each case chosen from the group formed by the hydrogen atom, alkyl, arylalkyl, aryl and alkyl aryl radicals and $R_2$ and $R_3$, which can be the same or different, are each chosen from within the group formed by alkyl, aryl alkyl, aryl and alkyl aryl radicals.

Tertiary olefins constitute a very important starting material for the preparation of certain chemical products and in particular polymers, so that it is essential to have very pure tertiary olefins.

It is known that by reacting an olefin or a mixture of olefins with a primary alcohol in the presence of an acid such as sulphuric acid, or a solid having an appropriate acidity, it is possible to obtain the corresponding ether or ethers. Moreover, the speed of said reaction is dependent on the operating conditions and also the nature of the radicals R, $R_1$, $R_2$ and $R_3$. It is possible to selectively react in an olefin fraction, such as a fraction obtained from thermal or catalytic cracking, tertiary olefins with at least one primary alcohol. The then formed tert.-alkyl-alkyl-ether can easily be separated from the olefins which have not reacted and then decomposed in order to again give the corresponding purified tertiary olefin.

The prior art describes catalytic processes for the production of tertiary olefins by the catalytic decomposition of the corresponding ethers. However, as this reaction is aided at high temperature, certain prior art catalysts lead to the formation of dialkyl ethers and water from the primary alcohol and therefore to a varying alcohol loss, which is prejudicial to the economics of a process in which the alcohol is normally recycled to the synthesis section of the tert.-alkyl-alkyl-ether.

Another undesired side reaction aided by certain prior art catalysts is the formation of oligomers from the olefin and which in particular lead to a significant drop in the purity of the olefin produced.

There has already been proposed a process for obtaining an olefin from the corresponding ether, which largely obviates the aforementioned disadvantages (U.S. Pat. No. 4,395,580). This process consists of operating with the aid of at one catalyst having optimized acid characteristics and in the presence of water vapor. This addition of water vapor makes it possible to increase the alcohol and olefin yields, but complicates the diagram of the process scheme and leads to significant extra costs.

The decomposition of tert. alkyl ethers on a silica-doped alumina-based catalyst is known (U.S. Pat. No. 4,006,198). However, this catalyst leads to the formation of dialkyl ethers on raising the reaction temperature.

It has already been proposed to prepare tertiary olefins by decomposing corresponding ethers in the presence of silica-based catalysts doped by alumina or an oxide of an element chosen from among chromium, beryllium, titanium, vanadium, manganese, iron, cobalt, zinc, zirconium, rhodium, silver, tin, antimony and boron (U.S. Pat. No. 4,254,296). However, as indicated by the authors of U.S. Pat. No. 4,254,296 in patent application WO 87/00166, these catalysts are difficult to prepare and have high production costs. In addition, they have a relatively short life, requiring an increase in the reaction temperature, whilst leading to the formation of undesired products.

Patent application WO 87/00166 describes improved catalysts for this application, constituted by silica modified by the addition of 0.1 to 1.5% by weight of alumina based on the silica. Although these catalysts are more stable than those previously referred to, they still suffer from a performance deterioration. Maintaining conversion above 70% makes it necessary to increase the temperature to 130° to 350° C. and, following 3000 hours operation, it is necessary to operate at temperatures of 250° C. in order to maintain said conversion, which leads to a methanol yield drop to below 99%.

SUMMARY OF THE INVENTION

The present invention makes it possible to largely obviate the aforementioned disadvantages by operating in the presence of at least one particular catalyst and preferably in the absence of water vapor, said catalyst being constituted by silica modified by the addition of at least one element or compound of an element chosen from the group constituted by lithium, rubidium, cesium, magnesium, calcium, strontium, barium, gallium and lanthanides (La, Ce, Pr, Nd, Pm, Sm, Eu, Gd, Tb, Dy, Ho, Er, Tm, Yb, Lu) and uranides (U, Np, Pu, Am), preferably from the group constituted by rubidium, cesium, magnesium, calcium, strontium, barium, gallium, lanthanum, cerium, praseodymium, neodymium and uranium and even more preferred manner from the group constituted by rubidium, magnesium, calcium, lanthanum and cerium and optionally by the supplementary addition of at least one element or compound of an element chosen in the group constituted by aluminium, titanium and zirconium.

The silica used preferably has, following the incorporation of the element or elements or compounds of element referred to hereinbefore and after an appropriate heat treatment, a specific surface of at least 100 $m^2/g$ and more particularly between 150 and 700 $m^2/g$.

The element or elements (or their compounds) added to the silica, which are also referred to herein as additional agents or elements or basic silica modifying agents or elements, can be introduced by using any known method, such as ion exchange, dry impregnation, mechanical mixing or grafting organometallic complexes. However, it is preferable in general to introduce them by impregnating the said basic silica with at least one solution containing the elements or compounds of elements which it is wished to add in the form of their salts or other organic or inorganic derivatives soluble in the chosen impregnation solvent.

Thus, a method for preparing the catalyst used in the invention e.g. consists of impregnating the silica support with at least one aqueous solution (or in at least one appropriate solvent) containing the modifying agent or agents which it is wished to introduce, said agents being used e.g. in the form of a halide, a nitrate, an acetate, an oxalate, a sulphate, a complex containing said agent or agents and e.g. a complex formed with oxalic acid and oxalates, with citric acid and citrates, tartaric acid and tartrates, with other polyacids and acid alcohols and their salts, acetyl acetonates and any other inorganic or organometallic derivative containing the chosen modifying agent or agents.

With the chosen modifying element or elements deposited on the silica, the product obtained is thermally treated, i.e. dried, by any known procedure, e.g. under an air or nitrogen flow and then calcined e.g. under an air or nitrogen flow at a temperature e.g. between 300° and 800° C.

The content, expressed by weight of oxide based on the weight of the silica, of the element or elements or compounds of elements deposited on the surface of the silica (and therefore contained in the catalyst) is normally between 0.01 and 35%, preferably between 0.05 and 25%.

The decomposition reaction of the ether or ethers according to the invention is carried out at a temperature generally between 100° and 500° C. and preferably between 130° and 350° C. If the decomposition of the ethers takes place with a good yield at atmospheric pressure, preference is generally given to operating at a pressure at least equal to that of the vapour tension of the olefin which it is wished to obtain at the condensation temperature used. It is usual to operate at a pressure between 0.11 and 2 MPa and preferably between 0.4 and 1.5 MPa.

The ether flow rate, expressed by liquid charge volume per catalyst volume and per hour (liquid hourly space velocity or SV) is generally between 0.1 and 200 and preferably between 0.7 and 30.

The process according to the invention is particularly suitable for obtaining in the pure state tertiary olefins of formula

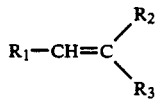

from the corresponding ethers of formula

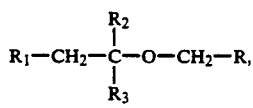

in which R and $R_1$, which can be the same or different, are each chosen within the group formed by the hydrogen atom, methyl, ethyl, n-propyl and isopropyl radicals and $R_2$ and $R_3$, which can be the same or different, are each chosen from within the group formed by the methyl, ethyl, n-propyl and isopropyl radicals.

The primary alcohol recovered after the decomposition of the ether preferably contains 1 to 6 carbon atoms.

The process according to the invention can more particularly apply to the decomposition of the methyl tert. butyl ether (MTBE) or ethyl tert. butyl ether (ETBE) with a view to obtaining pure isobutylene (and methanol or ethanol).

The decomposition reaction of the ethers into primary alcohols or tertiary olefins according to the process of the present invention is substantially quantitative and the alcohol and olefin recovery rate is close to 100%.

The following examples illustrate the invention without limiting the scope thereof.

EXAMPLE 1

Preparation of a catalyst A in accordance with that used in the invention.

50 g of silica with a specific surface of 250 m$^2$/g and a pore volume of 1.32 cm$^3$/g are contacted in a rotary mixer with an aqueous solution $S_1$ of 65 ml containing 35 g of magnesium nitrate hexahydrate, followed by the slow evaporation to dryness of the solution at 80° C.

The thus obtained impregnated silica is then dried for approximately 1 hour at 100° C. and then for approximately 16 hours at 150° C. and is finally calcined for approximately 3 hours at 600° C.

The catalyst A obtained has a specific surface of 220 m$^2$/g and contains 7.7% by weight MgO (based on the silica weight).

EXAMPLE 2

Preparation of a catalyst B in accordance with that used in the invention.

The preparation of the catalyst B differs from that described in Example 1 in that the aqueous solution $S_1$ is replaced by an aqueous solution $S_2$ of 65 ml containing 1.6 g of magnesium nitrate hexahydrate.

The catalyst B obtained has a specific surface of 245 m$^2$/g and contains 0.46% by weight of MgO (based on the silica weight).

EXAMPLE 3

Preparation of a catalyst C in accordance with that used in the invention.

An aqueous solution $S_3$ is prepared of 195 ml containing 67 g of magnesium nitrate hexahydrate. This solution is subdivided into three solutions $Z_1$, $Z_2$ and $Z_3$ of 65 ml each. 50 g of silica with a specific surface of 250 m$^2$/g and a pore volume of 1.32 cm$^3$/g are contacted in a rotary mixer with the solution $Z_1$ (stage a)) and then the solution is slowly evaporated to dryness at 80° C. (stage b)).

The thus obtained impregnated silica is then dried for approximately 1 hour at 100° C. (stage c)) and then for approximately 16 hours at 150° C. (stage d)) and is finally calcined for approximately 3 hours at 600° C. (stage e)).

The thus obtained modified silica is then contacted in a rotary mixer with the solution $Z_2$ (stage a)) and then again undergoes stages b) to e). Following this second impregnation, a third impregnation is carried out with solution $Z_3$ following stages a) to e).

The thus obtained catalyst C has a specific surface of 210 m²/g and contains 20% by weight MgO (based on the silica weight).

EXAMPLE 4

Preparation of a catalyst D in accordance with that used in the invention.

The catalyst A prepared in Example 1 is treated by an aqueous solution $S_4$ of 60 ml containing 1.4 g of aluminium nitrate nonahydrate and then the solution is slowly evaporated to dryness at 80° C.

The thus obtained solid is then dried for approximately 1 hour at 100° C. and then for approximately 16 hours at 150° C., followed by calcination for approximately 3 hours at 600° C.

The thus obtained catalyst D has a specific surface of 240 m²/g and contains 7.7% by weight MgO and 0.37% by weight $Al_2O_3$ (based on the silica weight).

EXAMPLE 5

Preparation of a catalyst E according to that used in the invention.

The preparation of the catalyst E differs from that described in Example 4 in that the aqueous solution $S_4$ is replaced by an aqueous solution $S_5$ of 60 ml containing 0.30 g of zirconyl nitrate dihydrate.

Catalyst E obtained has a specific surface of 235 m²/g and contains 7.7% by weight MgO and 0.27% by weight $ZrO_2$ (based on the silica weight).

EXAMPLE 6

Preparation of a catalyst F in accordance with that used in the invention.

The preparation of the catalyst F differs from that described in Example 1 in that the aqueous solution $S_1$ is replaced by an aqueous solution $S_6$ of 65 ml containing 6.8 g of lanthanum nitrate hexahydrate.

The catalyst F obtained has a specific surface of 210 m²/g and contains 4.6% by weight $La_2O_3$ (based on the silica weight).

EXAMPLE 7

Preparation of a catalyst G in accordance with that used in the invention.

The preparation of the catalyst G differs from that described in Example 1 in that the aqueous solution $S_1$ is replaced by an aqueous solution $S_7$ of 65 ml and containing 1.6 g of rubidium nitrate.

The catalyst G obtained has a specific surface of 247 m²/g and contains 2.0% by weight of $Rb_2O$ (based on the silica weight).

EXAMPLE 8

Catalyst H not in accordance with that used in the invention

Catalyst H is constituted by unmodified silica with a specific surface of 250 m²/g and a pore volume of 1.32 cm³/g (it corresponds to the starting material used in Examples 1 to 7).

EXAMPLE 9

Preparation of a catalyst I not in accordance with that used in the invention.

The preparation of the catalyst I differs from that described in Example 1 in that aqueous solution $S_1$ is replaced by an aqueous solution $S_9$ identical to the aqueous solution $S_4$ described in Example 4.

The catalyst I obtained has a specific surface of 250 m²/g and contains 0.37% by weight of $Al_2O_3$ (based on the silica weight).

EXAMPLE 10

Preparation of a catalyst J not in accordance with that used in the invention.

The preparation of the catalyst J takes place in accordance with the following operating procedure (corresponding to that described in U.S. Pat. No. 4,254,296). 40 g of ethyl orthosilicate are heated to 80° C. under nitrogen, then contacted with 100 ml of a 20% by weight aqueous tetrapropyl ammonium hydroxide solution under a nitrogen atmosphere and accompanied by stirring, the temperature being maintained at 80° C. When the mixture becomes homogeneous and clear, 4 g of beryllium nitrate tetrahydrate dissolved in 80 ml of ethanol and 1.5 g of soda dissolved in 10 ml of distilled water are added. A compact gel forms and to it is added distilled water in order to bring the total volume to 200 ml.

This is then heated to boiling accompanied by vigorous stirring in order to terminate the hydrolysis and evacuate the ethanol. The gel is then converted into a white powder. Distilled water is again added in order to top up the volume to 150 ml, followed by raising to a temperature of 155° C. for 17 days in an autoclave.

The solid formed is then separated by centrifuging, the cake is washed with distilled water and centrifuged four times, then dried at 120° C. in an oven and finally calcined for 16 hours at 550° C. under air scavenging.

The solid obtained is again washed three times by resuspending in an aqueous ammonium acetate solution at boiling point. The solid is then calcined at 550° C. for 6 hours.

The thus obtained catalyst J has a specific surface of 470 m²/g and contains 3.2% by weight BeO (based on the silica weight).

EXAMPLE 11

Preparation of a catalyst K not in accordance with that used in the invention.

50 g of silica with a specific surface of 60 m²/g and a pore volume of 0.50 cm³/g are contacted in a rotary mixer with an aqueous solution $S_{11}$ of 25 ml containing 15 g of magnesium nitrate hexahydrate and then the solution is slowly evaporated to dryness at 80° C.

The thus obtained impregnated silica is then dried for approximately 1 hour and then for approximately 16 hours at 150° C., finally being calcined for approximately 3 hours at 600° C.

The thus obtained catalyst K has a specific surface of 50 m²/g and contains 4.6% by weight MgO (based on the silica weight).

EXAMPLE 12

Preparation of a catalyst L not in accordance with that used in the invention.

The preparation of the catalyst L differs from that described in Example 3 in that the aqueous solution $S_3$ is replaced by an aqueous solution $S_{12}$ of 195 ml containing 130 g of magnesium nitrate hexahydrate.

The catalyst L obtained has a specific surface of 200 m²/g and contains 40% by weight MgO (based on the silica weight).

EXAMPLE 13

According to the invention

Catalysts A to G are introduced into a reactor, treated for 2 hours under dry nitrogen and then tested in the decomposition reaction of methyl tert. butyl ether (MTBE) in methanol and isobutylene under the following operating conditions:

| Temperature: | 170 to 250° C. |
|---|---|
| Pressure: | 0.7 MPa |
| SV: | 1 or 2 h$^{-1}$ |

Table 1 summarizes the results obtained with these different catalysts with the indicated temperature (T) and SV conditions. Reference is also made to the dimethyl ether (DME) concentrations produced (ppm).

TABLE 1

| Catalyst | T (°C.) | SV (h$^{-1}$) | Test duration (h) | MTBE conversion (%) | Methanol recovered (% by weight) | Isobutylene recovered (% by weight) | DME produced (ppm) |
|---|---|---|---|---|---|---|---|
| A | 170 | 1 | 200 | 79 | 99.9 | 99.7 | 60 |
| A | 170 | 2 | 200 | 75.0 | 100.0 | 99.9 | 45 |
| A | 220 | 2 | 1000 | 74.5 | 99.9 | 99.9 | 376 |
| A | 250 | 2 | 5000 | 78.2 | 99.3 | 99.9 | 1450 |
| B | 170 | 2 | 200 | 69.5 | 98.9 | 99.5 | 2050 |
| C | 170 | 2 | 200 | 73.0 | 100.0 | 99.9 | 35 |
| D | 170 | 2 | 200 | 82.0 | 99.8 | 99.8 | 147 |
| E | 170 | 2 | 200 | 78.0 | 99.9 | 99.8 | 68 |
| F | 170 | 2 | 100 | 72.8 | 99.9 | 99.9 | 56 |
| G | 170 | 2 | 100 | 73.6 | 99.8 | 99.7 | 173 |

EXAMPLE 14

Comparative

Catalysts H to L are introduced into a reactor, treated for 2 hours under dry nitrogen and then tested in the decomposition reaction of methyl tert. butyl ether (MTBE) in methanol and isobutylene at a pressure of 0.7 MPa.

Table 2 gives the operating conditions used and the results obtained.

The comparison between Tables 1 and 2 shows that better results are obtained with the catalysts in accordance with those recommended by the invention.

TABLE 2

| Catalyst | T (°C.) | SV (h$^{-1}$) | Test duration (h) | MTBE conversion (%) | Methanol recovered (% by weight) | Isobutylene recovered (% by weight) | DME produced (ppm) |
|---|---|---|---|---|---|---|---|
| H | 170 | 2 | 200 | 51.8 | 98.6 | 99.5 | 2550 |
| I | 170 | 2 | 200 | 63.0 | 99.8 | 99.5 | 150 |
| I | 220 | 2 | 1000 | 51.1 | 99.2 | 99.7 | 1500 |
| J | 170 | 2 | 200 | 64.6 | 99.7 | 99.4 | 650 |
| J | 220 | 2 | 1000 | 63.7 | 99.5 | 99.2 | 1000 |
| K | 170 | 2 | 200 | 41.0 | 99.8 | 99.5 | 2130 |
| L | 170 | 2 | 200 | 56.0 | 99.9 | 99.9 | 50 |

We claim:

1. A process for obtaining at least one tertiary olefin of formula

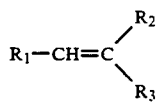

by decomposition of the corresponding ether of formula

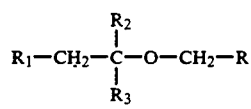

in which R and R$_1$, which can be the same or different, are each chosen from within the group formed by hydrogen, the alkyl, arylalkyl, aryl and alkylaryl radicals, and R$_2$ and R$_3$, which can be the same or different, are each chosen from within the group formed by the alkyl, arylalkyl, aryl and alkylaryl radicals, in the presence of a catalyst consisting essentially of silica modified by an additive consisting essentially of at least one element or compound of an element chosen from within the group consisting of rubidium, magnesium, calcium, strontium, barium, and lanthanum, wherein the content, expressed by weight of oxide based on the silica weight, of said element or elements or said compounds of elements contained in said catalyst is between 0.01 and 35%, wherein said silica, following the incorporation of said element or elements or said compounds of elements, has a specific surface of at least 100 m²/g, and wherein the modification is conducted by impregnating into the silica an aqueous solution of said additive, and resultant silica is dried and calcined.

2. A process according to claim 1, wherein working takes place in the absence of water vapor.

3. A process according to claim 1, wherein said catalyst is constituted by silica modified by the addition of at least one element or compound of an element chosen from within the group constituted by rubidium, magnesium, calcium, lanthanum.

4. A process according to claim 1, wherein said content of said element or elements or said compounds of elements contained in the catalyst is between 0.05 and 25%.

5. A process according to claim 1, wherein said silica, following the incorporation of said element or elements, or said compounds of elements, has a specific surface of between 150 and 700 m$^2$/g.

6. A process according to claim 1, wherein working takes place under a pressure between 0.11 and 2 MPa, at a temperature between 100° and 500° C. and with an hourly liquid space velocity between 0.1 and 200 liquid charge volumes per catalyst volume and per hour.

7. A process according to claim 1, wherein working takes place under a pressure between 0.4 and 1.5 MPa, a temperature between 130° and 350° C. and an hourly liquid space velocity between 0.7 and 30 liquid charge volumes per catalyst volume and per hour.

8. A process according to claim 1, wherein R and R$_1$, which can be the same or different, are each chosen from within the group formed by the hydrogen, methyl, ethyl, n-propyl and isopropyl radicals and R$_2$ and R$_3$, which can be the same or different, are each chosen from within the group formed by the methyl, ethyl, n-propyl and isopropyl radicals.

9. A process according to claim 1, wherein the said ether is methyl tert. butyl ether and said tertiary olefin is isobutylene.

10. A process according to claim 1, wherein said ether is ethyl tert. butyl ether and said tertiary olefin is isobutylene.

11. A process according to claim 7, wherein said silica, following the incorporation of said element or elements or said compounds of elements, has a specific surface of between 150 and 700 m$^2$/g.

12. A process according to claim 11, wherein the silica is further modified by the addition of magnesium or a compound thereof.

* * * * *